(12) United States Patent
Walsh

(10) Patent No.: US 7,981,101 B2
(45) Date of Patent: Jul. 19, 2011

(54) MEDICAL VIAL ADAPTER WITH REDUCED DIAMETER CANNULA AND ENLARGED VENT LUMEN

(75) Inventor: Mary K. Walsh, Raleigh, NC (US)

(73) Assignee: CareFusion 303, Inc., San Diego, CA (US)

( * ) Notice: Subject to any disclaimer, the term of this patent is extended or adjusted under 35 U.S.C. 154(b) by 379 days.

(21) Appl. No.: 11/325,831

(22) Filed: Dec. 30, 2005

(65) Prior Publication Data

US 2007/0156112 A1    Jul. 5, 2007

(51) Int. Cl.
*A61M 5/32*        (2006.01)
(52) U.S. Cl. .......................................... 604/411
(58) Field of Classification Search .................. 604/411, 604/414
See application file for complete search history.

(56) References Cited

U.S. PATENT DOCUMENTS

| | | | |
|---|---|---|---|
| 4,822,351 A | | 4/1989 | Purcell |
| 6,120,490 A | | 9/2000 | Neftel |
| 6,139,534 A | * | 10/2000 | Niedospial et al. ........... 604/411 |
| 6,544,246 B1 | | 4/2003 | Niedospial, Jr. |
| 2003/0229330 A1 | | 12/2003 | Hickle |
| 2005/0033265 A1 | * | 2/2005 | Engel et al. ................... 604/523 |

* cited by examiner

*Primary Examiner* — Melanie J Hand
(74) *Attorney, Agent, or Firm* — McDermott, Will & Emery

(57) ABSTRACT

A vented vial adapter for reconstitution of a medicament in a vial includes a vent lumen and a medicament lumen. The vent lumen has a cross-sectional area equal to or greater than that of the medicament lumen so that the fluid flow rate through the vent lumen is equal to or greater than that of the medicament lumen. As a result aerosols of the medicament outside the adapter are avoided as is the withdrawal of air bubbles from the vial as the reconstituted medicament is withdrawn from the vial. To maintain the diameter of the sharpened cannula of the vial adapter as small as possible, the vent lumen includes a concave wall facing the medicament lumen and a convex outer wall. In one embodiment, the vent lumen is in the shape of a polygon.

30 Claims, 9 Drawing Sheets

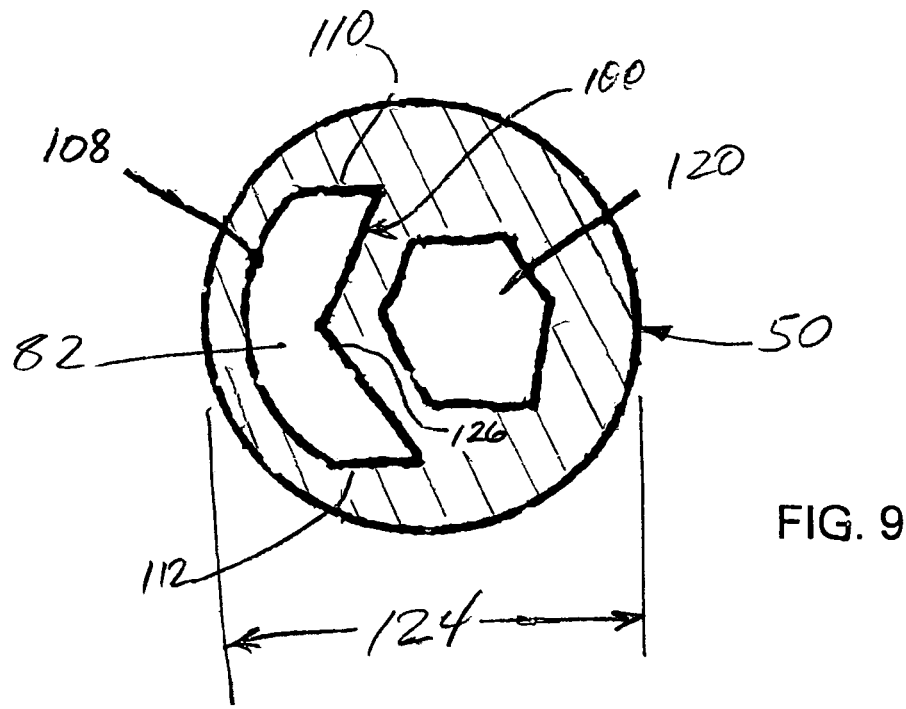
FIG. 9
FIG. 11
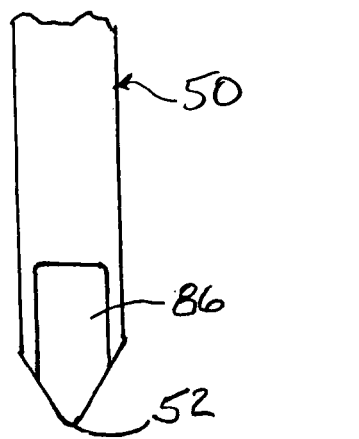
FIG. 10
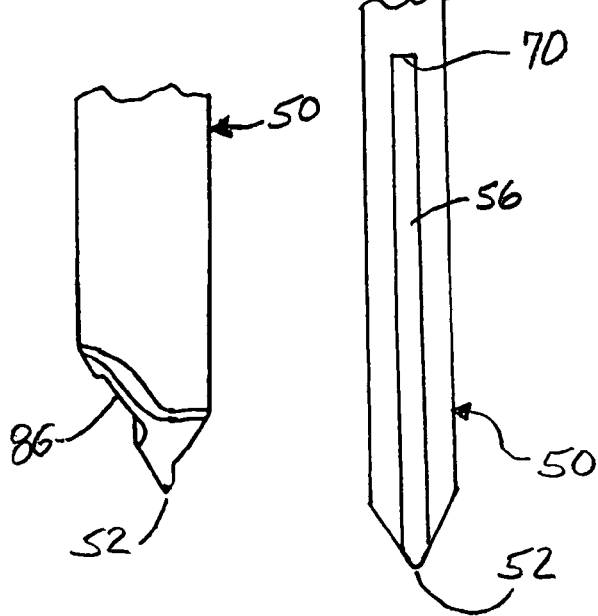
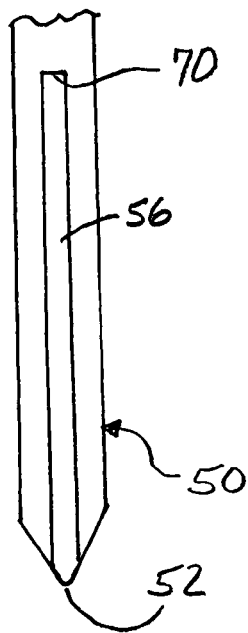
FIG. 12

MEDICAL VIAL ADAPTER WITH REDUCED DIAMETER CANNULA AND ENLARGED VENT LUMEN

BACKGROUND OF THE INVENTION

The invention is related generally to connectors of the type used in the handling and administration of medical fluids, and more particularly, to vial adapters useful for the rapid reconstitution and withdrawal of medicament from vials.

Access ports for injecting fluid into or removing fluid from a system, such as a drug vial, are well known and widely used. Conventional injection sites in drug vials generally involve a pierceable rubber stopper formed of an elastomeric material such as butyl rubber or the like, placed in the opening of the vial. A closure, typically formed of metal, is crimped over the rubber stopper and the flange of the vial to positively hold the stopper in place in the opening of the vial. The closure has an outer size, known as a "finish size." The closure also has an opening, or access port, through which the stopper and the vial opening may be accessed. A sharp cannula is inserted into the access port piercing the rubber stopper to position the distal, open end of the cannula past the rubber stopper to make fluid connection with the interior of the vial. In the case of certain medications, such as those used for chemotherapy or nuclear medicine, the rubber stopper is made thicker so that increased protection is provided against leakage.

Adapters have been found useful in that they can adapt the sharpened cannula that is placed into fluid communication with the vial to the connection device of another fluid container or fluid conduction device. For example, the adapter may include a female Luer fitting opposite the sharpened cannula to receive the nozzle of a syringe. The "adapter" therefore adapts the vial to the syringe, or adapts the sharpened cannula to the Luer-shaped nozzle of the syringe.

It has also been found useful in some applications to provide a means to attach or anchor the adapter to the vial to hold it in place while fluid communication between the vial and another device proceeds so that inadvertent disengagement of the adapter from the vial does not occur. For example, the adapter may have arms that engage the neck or flange of the vial and hold the adapter in place on the vial. Other means include a shroud that fits around the outside of the vial closure and snaps onto the vial closure under the crimped retaining cap thereby grasping the vial neck flange and the underside of the closure.

It has also been found useful in some applications to have a valve placed in the adapter to result in a closed system. The valved adapter permits engagement of the sharpened cannula with the contents of the vial without leakage of fluid from the vial through the adapter. Then when the second fluid device has been prepared, it can be connected to the adapter thereby activating the valve that then permits fluid flow between the vial and second fluid device.

Vials made of glass or polymeric materials, the walls of which are non-collapsible, require an air inlet when medical fluid is withdrawn therefrom to prevent the formation of a partial vacuum therein. Typically, vials containing a medical fluid are closed by rubber stoppers which are pierced by a spike having both a medicament fluid lumen and a vent lumen therein. The vent lumen may contain a filter to prevent the entry of particulate matter or bacteria into the vial during the medicament withdrawal process. Another purpose of the filter may include the prevention of venting to the outside atmosphere any atomized medicament or aerosols that are formed within the vial during the reconstitution process.

Many medicaments are prepared, stored, and supplied in dry or lyophilized form. Such medicaments must be reconstituted at the time of use by the addition of a diluent thereto. Various methods of adding the diluent to the dry or lyophilized medicament have been used over the years. One method that is commonly used is the vial adapter technique in which the diluent that may be contained in a bottle or a syringe is connected to the vial adapter which has a sharpened cannula. Once connected to the diluent, the sharpened cannula is then forced through the rubber septum closure of the vial to communicate the diluent to the dry or lyophilized medicament in the vial. After reconstitution, the liquid is usually returned to the intravenous solution bottle or syringe, or other container for administration to the patient through an intravenous ("IV") administration set. With some vial adapters, this technique is unsatisfactory because both the dry or lyophilized material and the diluent can be exposed to ambient airborne bacterial contamination if a filter is not present in the vial adapter.

During the reconstitution process, it is desirable to avoid contamination of the surrounding air through formation of aerosols or drops. This is possible during the injection of the diluent into the vial. This air contamination can lead to problems among other things in the form of allergic reactions in the exposed personnel, especially when it is a question of cytotoxic drugs, chemotherapeutic drugs, anesthetics, media containing isotopes, and allergy inducing substances of various kinds.

It would be desirable to provide a vented vial adapter for use with non-collapsible containers that is designed to prevent aerosolizing of liquid material as reconstitution occurs. It is desirable for the person performing the procedures to avoid contacting the medications, especially the inhalation of aerosolized medications. A vial adapter with sufficient venting and filtering is necessary to avoid such aerosolizing.

It is also desirable to provide a vial adapter that enables the rapid withdrawal of reconstituted medication from a vial. Clinicians are extremely busy people and systems and devices that can safely speed up the medication administration processes are desirable. Once reconstituted, it is desirable to withdraw the medicament from the vial as rapidly as possible so that administration to the patient can proceed. However, it the venting of the vial does not have the same or better flow capacity than the withdrawal flow rate of the reconstituted medicament by the syringe, air bubbles may be drawn into the syringe with the medicament. This is because a relatively high partial vacuum level may be created inside the vial due to inadequate venting. This high level of partial vacuum then can cause any air that is introduced to the vial to be drawn immediately into the syringe, instead of remaining in the vial. While patients can tolerate receiving a certain level of air from an IV medical fluid line, too high of a level of air can result in an air embolism with an adverse effect on the patient. Hence, a sufficient vial venting system is desirable.

Some manufacturers have attempted to create larger venting systems in vial adapters having sharpened cannulae. As an example, a venting lumen through the sharpened cannula and the body of the adapter has been formed so that the flow of venting air into the vial is equal to or greater than the flow of reconstituted medicament out of the vial. However in at least one manufacturer's system, the sharpened cannula had such a large outer diameter to accommodate the enlarged vent lumen that it became difficult to force such a large cannula through the rubber septum of a vial. It was even more difficult to force through the thickened stopper of a vial containing a chemotherapy medication. Increased strength is needed on the part of the clinician to pierce the septum, which is also undesirable. In this prior design and in others, reducing the diameter of the sharpened cannula while retaining the enlarged size of the vent lumen would result in a weakened cannula that can fracture or break off during the process of piercing the vial's stopper.

Hence, those skilled in the art have recognized a need for a vial adapter having improved venting capability while at the same time providing a sharpened cannula that remains as small as possible yet has enough strength to pierce a vial septum without breaking or fracturing. The present invention fulfills these needs and others.

SUMMARY OF THE INVENTION

Briefly and in general terms, the present invention is directed to a system and a method for use in reconstituting medicaments in rigid vials that provides a venting lumen having a flow rate as great as or greater than the lumen through which the medicament flows. In accordance with a system of the invention, an increased area of the air vent and a conforming shape of that vent allows a flow rate as great as or greater than the medicament lumen, while at the same time maintaining a smaller diameter of the sharpened cannula of the vial adapter.

In accordance with aspects of the invention, there is provided a vial adapter for accessing a vial having a vial closure that includes a pierceable seal located over an opening of the vial, the adapter comprising a housing having an attachment device to engage the vial for secure mounting of the vial adapter to the vial, a body portion having a medicament port and a vent port with a medicament lumen leading to the medicament port and a vent lumen leading to the vent port, the medicament and vent lumina being separate from each other, and a cannula located within the housing having a sharpened tip for piercing the seal of the vial closure to provide access to vial contents, the cannula having a medicament lumen in fluid communication with the body medicament lumen and a vent lumen in fluid communication with the body vent lumen, the cannula medicament lumen and cannula vent lumen having respective openings disposed on the sharpened cannula, wherein the cannula vent lumen has an inner wall that has a generally concave cross-sectional shape, and wherein a length and cross-sectional size of the combination of the body vent lumen and cannula vent lumen are selected so that the flow rate of fluid through the body and vent lumina is at least as great as a flow rate of fluid through the combination of the body and cannula medicament lumina.

In a more detailed aspect, the generally concave cross-sectional shape of the inner wall of the cannula vent lumen comprises an angulation oriented toward an outer wall of the cannula vent lumen. Further, the outer wall of the cannula vent lumen has a generally convex cross-sectional shape. Yet further, the generally convex outer wall and generally concave inner wall are interconnected by two side walls. In more detail, the side walls are approximately straight but are non-radially oriented with respect to a longitudinal center line of the sharpened cannula. In even further detail, the generally concave cross-sectional shape of the inner wall of the cannula vent lumen comprises a complex curve.

In other aspects, the cross-sectional shape of the inner wall of the cannula vent lumen comprises linear portions forming an obtuse angle, the vertex of which faces an outer wall. The inner wall of the cannula vent lumen is oriented to face the cannula medicament lumen whereby the cannula vent lumen may be positioned closer to the cannula medicament lumen within the cannula to result in a smaller diameter cannula yet a vent lumen that is at least as large as the medicament lumen.

In the aspect where the cross-sectional shape of the cannula medicament lumen is generally circular, the cannula vent lumen may be positioned closer to the cannula medicament lumen within the cannula to result in a smaller diameter cannula yet a vent lumen that is at least as large as the medicament lumen. In yet another aspect, the opening of the cannula vent lumen on the cannula is closer to the sharpened tip than is the opening of the cannula medicament lumen on the cannula.

Turning now to yet further aspects in accordance with the invention, the vial adapter further comprises a needle free valve disposed at the medicament port of the body adapted to control the flow of fluid through the medicament lumina. The vial adapter further comprises a filter disposed at the vent port of the body adapted to control the flow of fluid through the vent lumina. In one aspect, the filter comprises an hydrophilic filter and in another aspect, the filter comprises an anti-bacterial filter.

In another aspect, the cannula medicament lumen comprises a cross-sectional shape in the form of a polygon having the inner wall, an outer wall, and at least one side wall interconnecting the inner and outer walls. The polygon cross-sectional shape of the cannula vent lumen comprises the inner wall facing the medicament lumen wherein the concave shape is formed by a complex curve. The cannula medicament lumen is located at a longitudinal centerline of the sharpened cannula and the outer wall of the cannula vent lumen has a generally convex cross-sectional shape. The generally convex outer wall and generally concave inner wall are interconnected by two side walls that are approximately straight but are non-radially oriented with respect to a longitudinal center line of the sharpened cannula. An open channel or cannula slot is formed in the sharpened cannula leading from approximately the sharpened tip to the medicament opening to channel fluid through the medicament opening in the cannula.

A method for accessing a vial having a vial closure that includes a pierceable seal located over an opening of the vial is provided in accordance with aspects of the invention. The method comprises piercing the seal with a sharpened cannula having a medicament lumen and a vent lumen separate from each other wherein the cannula vent lumen has an inner wall having a generally concave shape such that it may be positioned closer to the medicament lumen, and the size and length of the vent lumen selected so that the flow rate of fluid through the vent lumen is at least as great as a flow rate of fluid through the medicament lumen, mounting a housing having an attachment device to the vial to secure the vial adapter to the vial and the sharpened cannula through the seal, the sharpened cannula being disposed within the housing, and communicating fluid through the sharpened cannula and through a body portion that is in fluid communication with the cannula, the body portion having a body medicament lumen in fluid communication with the cannula medicament lumen and having a medicament port, and a body vent lumen in fluid communication with the cannula vent lumen and having a vent port, the body medicament and vent lumina being separate from each other.

These and other aspects, features, and advantages of the present invention will become apparent from the following detailed description of the preferred embodiments which, taken in conjunction with the accompanying drawings, illustrate by way of example the principles of the invention.

BRIEF DESCRIPTION OF THE DRAWINGS

FIG. 9 is an alternate embodiment of the cross-sectional shapes of the medicament lumen and the vent lumen in the cannula showing their close proximity to one another yet showing an enlarged cross-sectional area of the vent lumen to result in a reduced outer diameter of the cannula while the vent lumen flow capacity is as great as or greater than the flow capacity of the medicament lumen; and FIGS. 10 through 12 show rotated side views of the cannula showing the sharp tip in all views, and the vent opening in the cannula in FIGS. 10 and 11 rotated ninety degrees, and the open channel or slot for the medicament opening in FIG. 12.

DETAILED DESCRIPTION OF PREFERRED EMBODIMENTS

Figure 1:
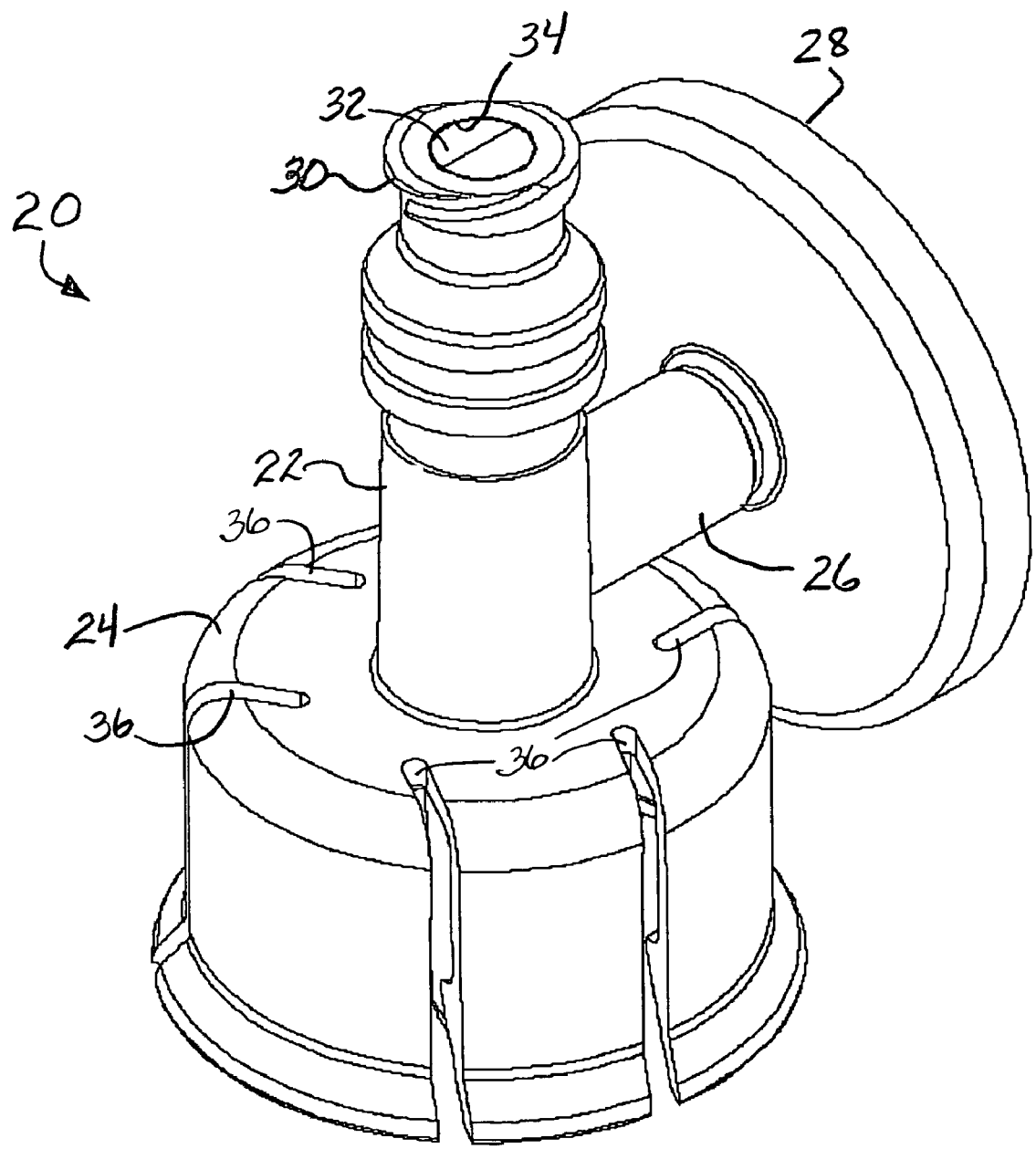
FIG. 1 is a perspective view of vented vial adapter looking down at a needle free valve connector forming a medicament port through which another container may be connected to the adapter, such as syringe, and through which diluent may be added to a vial and reconstituted medicament withdrawn from the vial; the vial adapter also having a side air vent arm and port at which a large chemotherapy filter is mounted.

Referring now to the drawings in more detail in which like reference numerals refer to like or corresponding elements among the views, there is shown in FIG. 1 a view of a vial adapter 20 in accordance with aspects of the invention. The vial adapter comprises a body portion 22, a housing 24, a vent arm 26 at a ninety degree angle to the longitudinal axis of the body portion, a filter device 28, and a needle free connector 30 having an internal valve 32, and a female Luer connection port 34. Such a needle free connector may take different forms. One such connector is the SmartSite valve connector from the ALARIS Products division of Cardinal Health. Details on the construction and operation of such a connector are located in U.S. Pat. No. 5,676,346 to Leinsing, incorporated herein by reference. It will be noted that the housing includes slots 36 that enable the housing to snap over a vial. The filter 28 in the case of FIG. 1 is enlarged for use with chemotherapy medications where more protection is needed. In this case, the filter paper used in the filter comprises 0.2 micron filter paper to prevent aerosols from reaching the atmosphere outside the adapter during reconstitution of the medication in the vial. The filter housing is colored yellow in one embodiment. The filter stem is firmly mounted within the vent arm 26.

Figure 2:
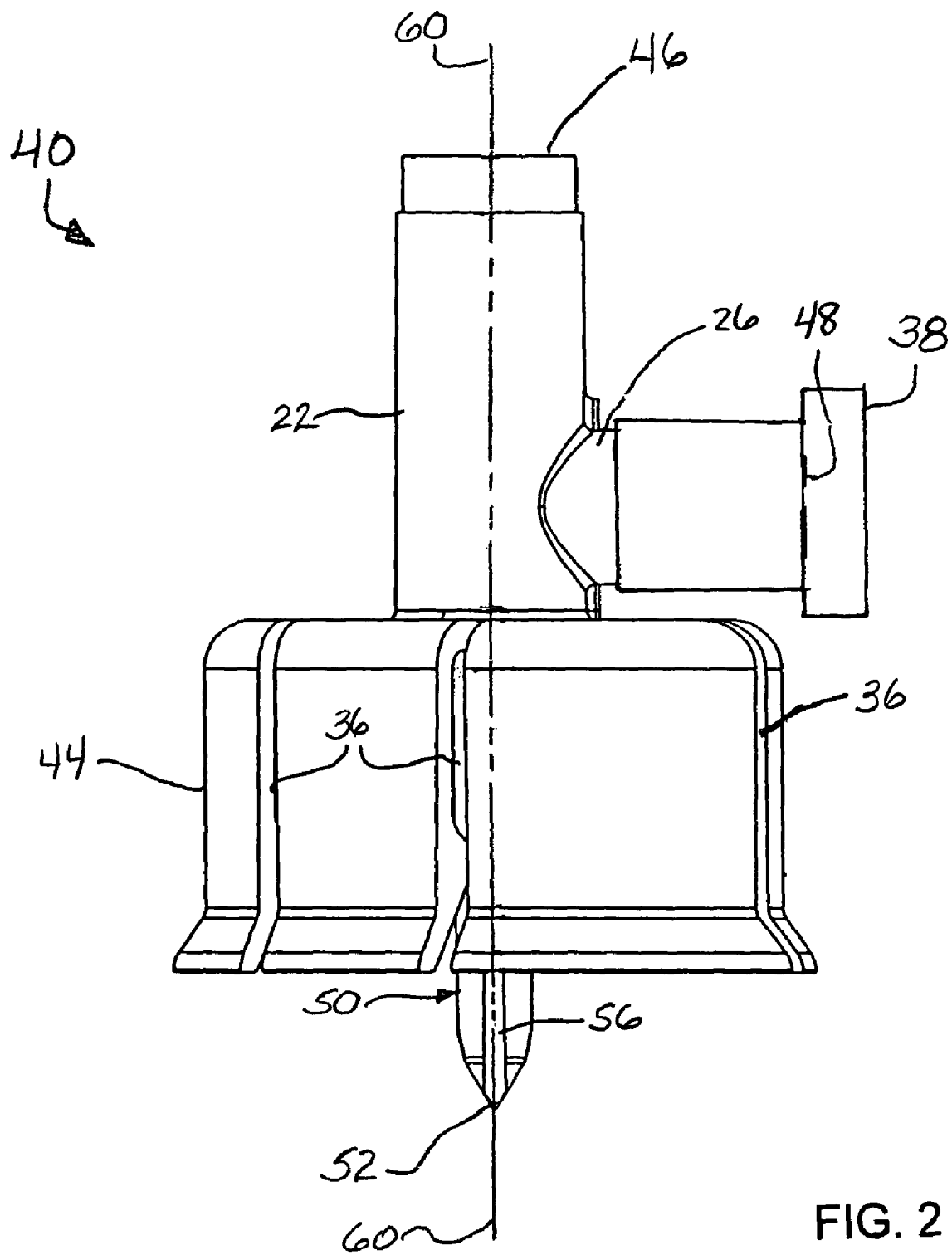
FIG. 2 provides a side view of the vial adapter of FIG. 1 with the needle free connector removed at the medicament port and with a different filter mounted to the vent arm, showing a cannula having a sharp tip and the slotted housing for attaching the vial adapter to a vial and thereby securely mounting the vial adapter to the vial.

Turning now to FIG. 2, a vial adapter 40 is shown without the needle free valve of FIG. 1 and with a different filter 38. In this case the filter is used more for the prevention of bacteria entering the vial during reconstitution and withdrawal and includes 3.0 micron filter paper. In one embodiment, the filter housing is colored white.

As in FIG. 1, the vial adapter of FIG. 2 has a body portion 22 and a housing 44 or attachment device for engaging a vial for secure mounting of the vial adapter to the vial. It also has a medicament port 46, a vent port 48, and a cannula 50 with a sharpened tip 52. Slots 36 formed in the housing permit the housing to flex outward to receive a vial. In this view, a cannula slot 56 or open channel for the medicament opening can be seen. The cannula is relatively long in this case so that it can accommodate the thicker stoppers of vials used for storage and reconstitution of chemotherapy medications and nuclear medicine. Consequently, the medicament opening is farther removed from the vent opening. Due to the location of the medicament opening in the cannula, as will be seen in another figure, the open channel 56 is formed in the cannula to guide fluid to the medicament opening and to permit an acceptable flow rate of the medicament. The adapter also has a vent arm 26. Also shown is a longitudinal axis 60 through the body portion, the housing, and the sharpened cannula. Although this embodiment does not include a needle free valved connector, such as that shown in FIG. 1, such a connector with an internal valve can be mounted at the medicament port over the body portion. In this case, the filter stem is mounted over the vent arm and is firmly secured thereon.

Figure 3:
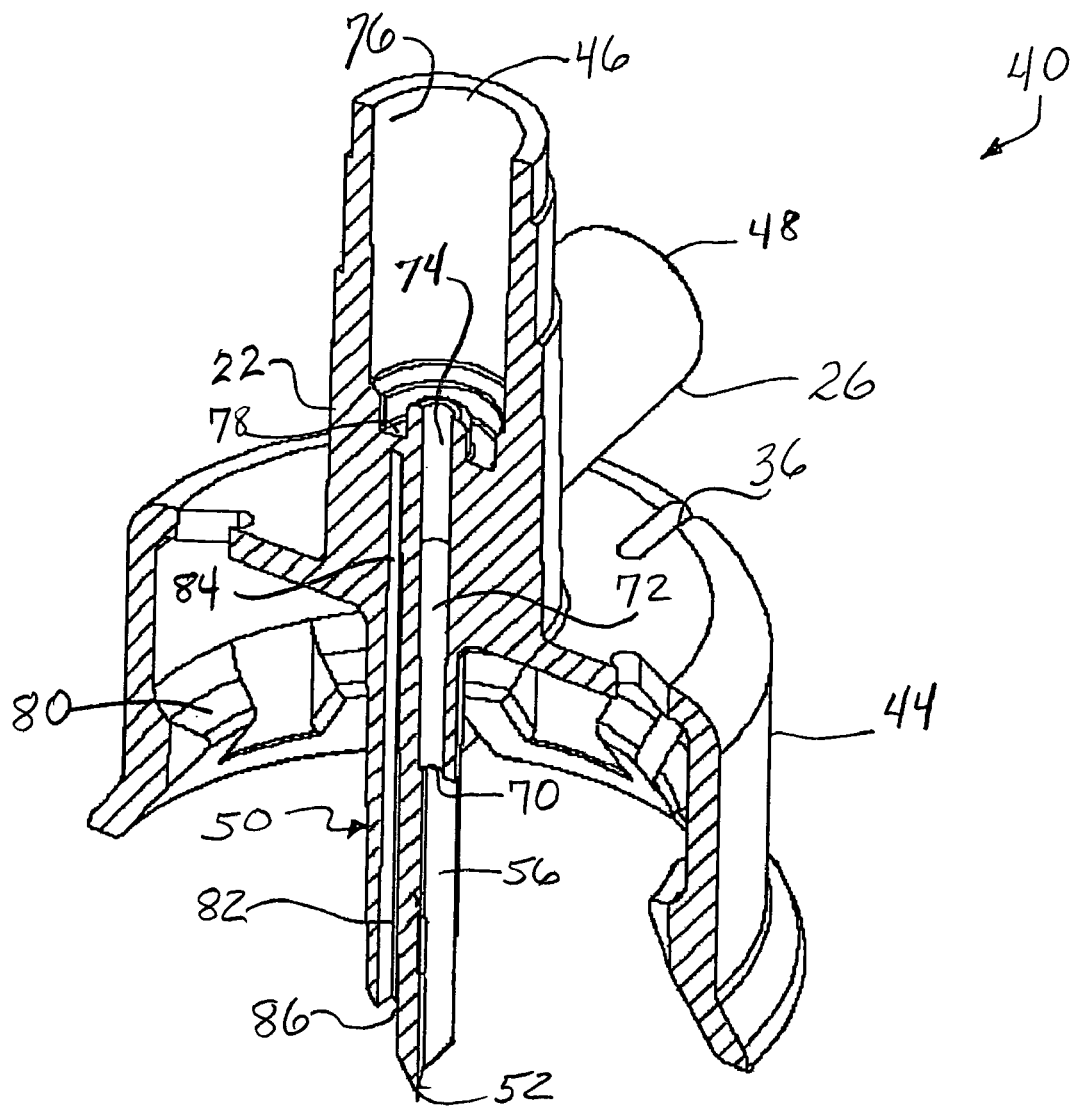
FIG. 3 illustrates a perspective, cross-sectional view of the vial adapter of FIGS. 1 and 2 with the needle free valve removed from the medicament port and the filter removed from the vent port, showing the medicament lumen through the sharpened cannula, the medicament lumen through the body portion, and a limited view of the vent lumina through the sharpened cannula and body portion.

In the partial cross-sectional perspective view of FIG. 3, showing the same vial adapter 40 as shown in FIG. 2, the medicament opening 70 in the sharpened cannula 50 can be seen as well as the exterior slot 56 formed in the cannula for that opening. The medicament opening is part of the medicament lumen 72 through the sharpened cannula and the medicament lumen 74 through the body portion 22. The body medicament lumen is in fluid communication with the medicament port 46 in the body portion. Prior to the medicament port, an enlarged cavity 76 is formed in the body portion. In this cavity, a groove 78 has been formed that may be used to mount a piston, such as that of a SmartSite valved connector, described and shown previously. Also shown in FIG. 3 is an attachment device 80 in the form of claws for grasping the underside of a vial flange to securely mount the vial adapter to the vial.

The view of FIG. 3 permits closer inspection of the medicament opening 70 in the cannula 50. It can be seen that the medicament opening is approximately perpendicular to the longitudinal axis of the cannula. To allow enough access to the opening 70 so that an adequate medicament flow rate can be obtained, the open channel or slot 56 has been formed in the side of the cannula from the sharp tip 52 to the medicament opening 70 so that more fluid may flow through the medicament opening.

Although not shown clearly, the cannula vent lumen 82 and body vent lumen 84 can be seen. They are separate from the respective cannula medicament lumen and body medicament lumen. The vent cannula opening 86 is visible at the sharpened tip 52 of the cannula 50.

Figure 4:
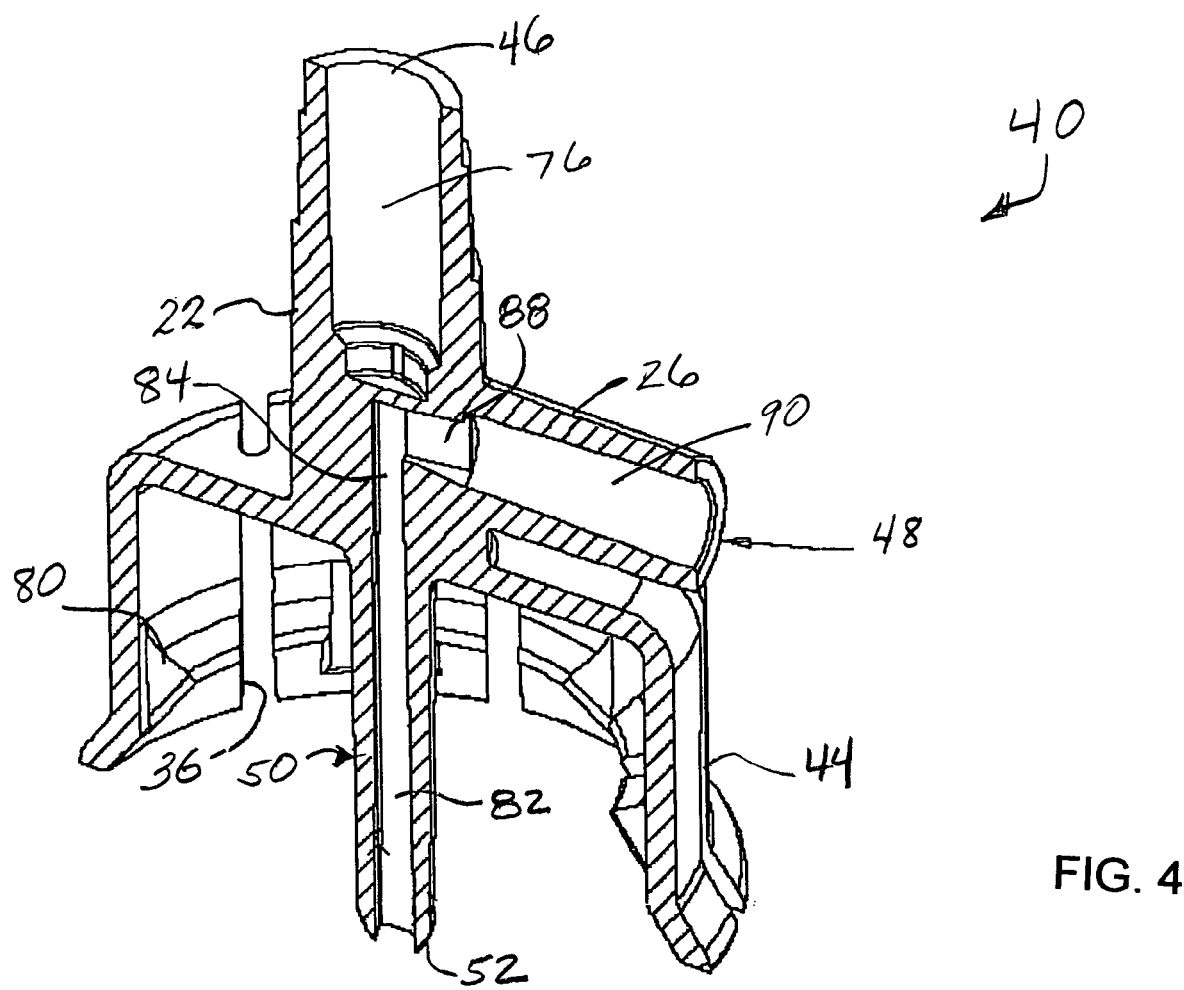
FIG. 4 is a perspective, cross-sectional view of the vial adapter of FIG. 3 rotated so as to show with more clarity the vent lumina of the sharpened cannula and the body portion, and showing the vent arm and its interconnection with the vent lumina in the adapter.
Figure 5:
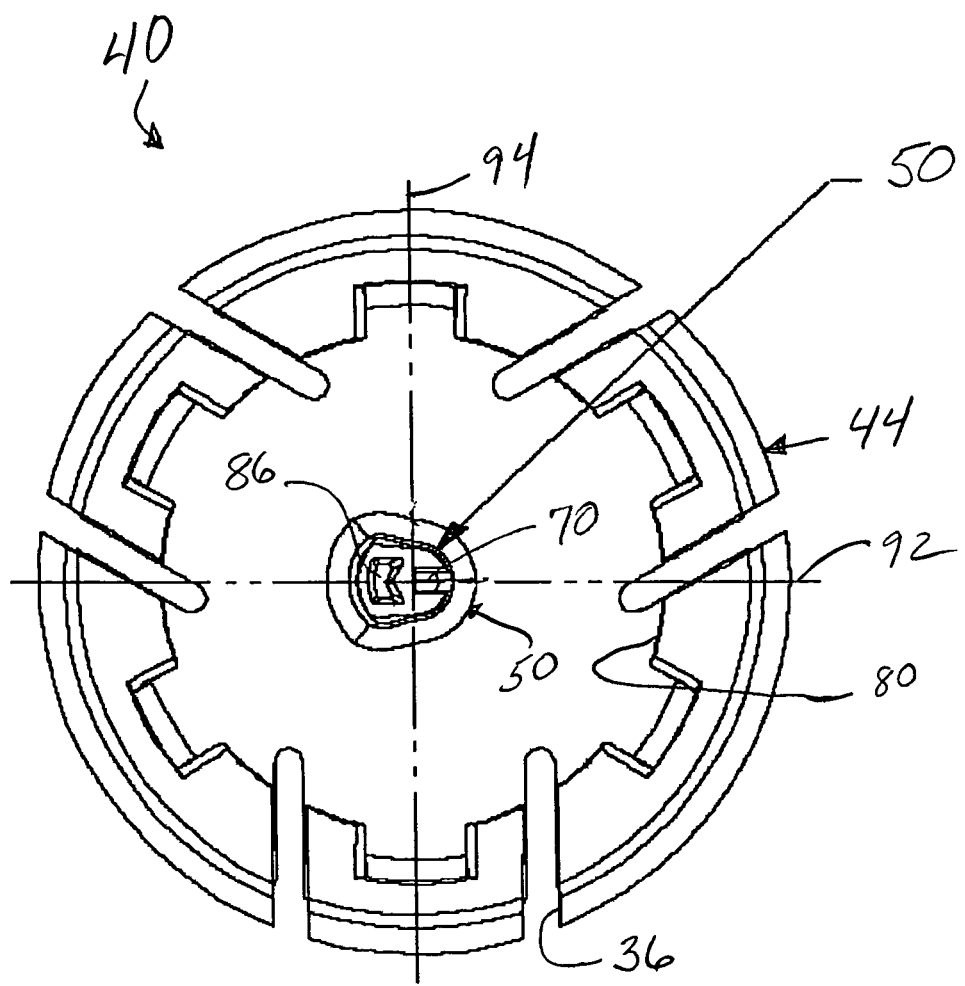
FIG. 5 is a bottom view of the vial adapter of FIGS. 1 through 4 showing a view of the sharp tip of the cannula revealing the openings of the vent and medicament lumina.
Figure 6:
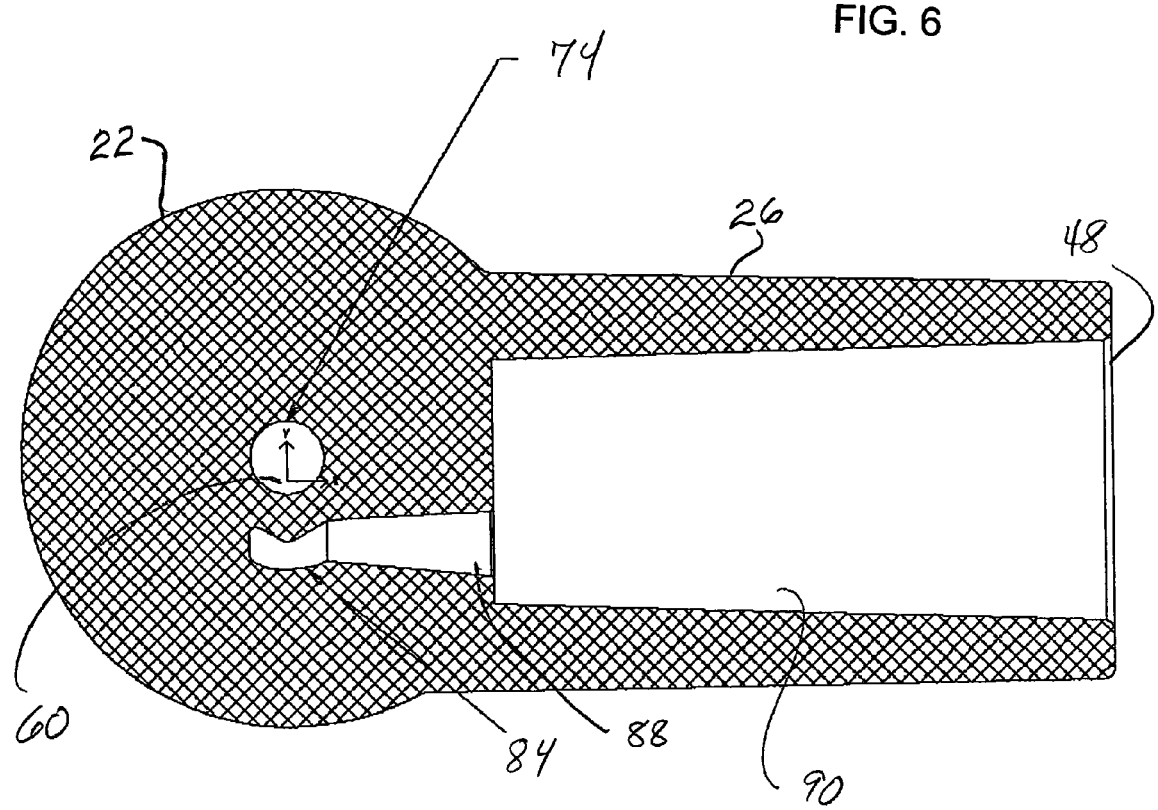
FIG. 6 is a cross-sectional view of the body portion showing the locations of the medicament and vent lumina and their respective cross-sectional shapes.
Figure 7:
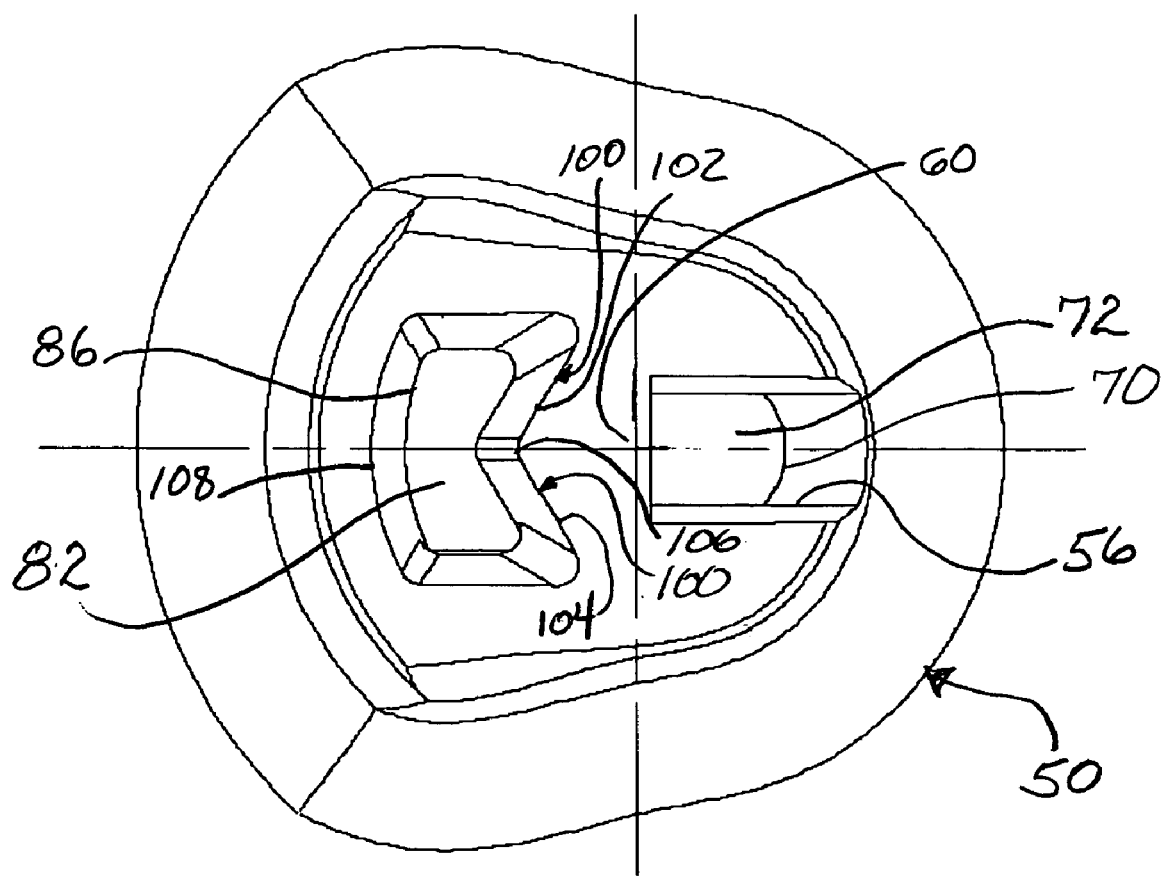
FIG. 7 is an enlarged bottom view of just the cannula showing further detail of the openings of the vent and medicament lumina in the cannula and the open longitudinal slot in the cannula leading to the medicament opening.
Figure 8:
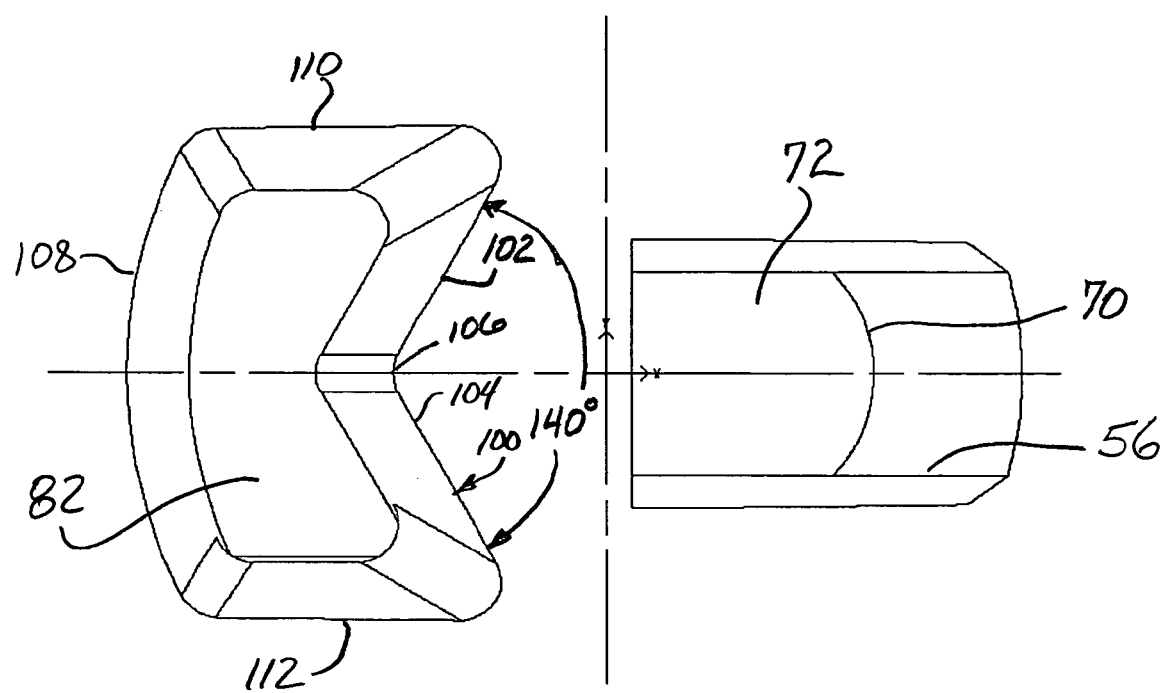
FIG. 8 is an enlarged view of the vent and medicament openings of the respective lumina in the cannula showing their respective shapes in this embodiment and how the outer diameter of the cannula is reduced while the area of the vent lumen is increased for greater venting of a vial, the figure also showing the obtuse angle of the angulation of the inner wall of the vent lumen.

FIG. 4 presents a clearer view of the cannula vent lumen 82 and body vent lumen 84. It will be noted that the body portion 22 includes a right angle vent lumen portion 88 leading to a vent cavity 90 similar to the medicament cavity 76. Although not shown in this view, the vent cavity may house a vent filter, such as an hydrophobic or anti-bacterial, or other, filter similar or identical to those shown in FIGS. 1 and 2.

FIG. 5 presents a view of the bottom of the vial adapter 40. Shown is the vent opening 86 and the medicament opening 70 in the sharpened cannula 50. Centerlines 92 and 94 are shown. The medicament opening and the vent opening reside on a common centerline 92 in this embodiment. The intersection of the centerlines marks the longitudinal axis of the vial adapter, as shown in FIG. 2. It will be noted that part of the medicament opening resides on that longitudinal axis.

FIG. 6 presents a cross-section view of the body medicament lumen 74, the body vent lumen 84, and the vent cavity 90 located in the vent arm 26. The right angle portion 88 of the body vent lumen is shown as is the vent cavity 90 and vent port 48 in the vent arm 26. The figure also shows the longitudinal axis 60 at the intersection of the "X" and "Y" axes. It will be noted that in this embodiment, the cross-sectional shape of the body medicament lumen 74 is circular and is located on the longitudinal axis although it is not centered on the axis. On the other hand, the cross-sectional shape of the body vent lumen 84 is in general a polygon having four sides, one of which is generally concave, facing toward the medicament lumen 74, and the opposite of which is convex, facing away from the medicament lumen.

Turning now to FIGS. 7 and 8, an enlarged view of the cannula vent lumen 82 can be examined. In this embodiment, the lumen has the polygon shape as shown in FIG. 6. The inner wall 100 is generally concave in shape, although in the embodiments of FIGS. 7 and 8, the concavity is created by two relatively straight segments 102 and 104 meeting at a vertex 106 to form an obtuse angle of 140 degrees. This effectively results in an angulation 106 in the direction of the outer wall 108 of the cannula vent lumen. As is apparent, the outer wall 108 in this embodiment is generally convex in form. The slot 78 formed in the cannula leading to the medicament opening 72 is also shown. Although only partially shown, the medicament opening is circular in cross-sectional shape, as shown in FIG. 6.

The polygon of FIG. 8 also includes sides 110 and 112 that are generally straight in this embodiment. Additionally, they are not located on radii from the longitudinal center line 60 and so may be referred to as non-radial. Although there are two side walls and four walls in total for the vent lumen of FIG. 8, more or fewer walls may be used. The partial coverage of the medicament opening 70 by the open channel or slot 56 also can be more clearly seen. The slot effectively provides access to the medicament opening from inside the vial. As a result of the configuration shown however, the vent lumen 82 has been moved closer to the medicament lumen 72 resulting in a smaller outer diameter of the cannula 50. Although the outer diameter of the cannula is smaller, the cross-sectional area of the vent lumen is equal to or greater than the medicament lumen 72 so as to result in an equal or greater flow rate through the vent lumen than through the medicament lumen. Such a feature will lower the risk of aerosolizing the medicament in a vial as discussed above in the Background section and will enable rapid withdrawal of reconstituted medicament from the vial.

FIG. 8 also more clearly shows that the open channel or slot 56 feeding the medicament lumen 72 partially covers the medicament lumen opening 70. The length and depth of this slot results in a greater flow rate of fluid through the medicament opening and lumen.

FIG. 9 presents a cross section of an alternate embodiment in which the cannula medicament lumen 120 has a cross-sectional shape of a hexagon although the cannula vent lumen 82 continues to have the shape of polygon, similar or identical to that shown in FIGS. 7 and 8. Similarly to the foregoing figures, the angulation 126 of the inner wall 100 of the cannula vent lumen is directed to the outer wall 108 of the vent lumen. Such a configuration allows the vent lumen to be positioned more closely to the medicament lumen resulting in a smaller outer diameter 124 for the cannula 50. The cannula vent lumen is somewhat "wrapped around" the cannula medicament lumen; however, the cross-sectional area of the vent lumen is equal to or greater than that of that of the medicament lumen resulting in a vent flow rate that is equal to or greater than the medicament flow rate. As in the previous figures, the vent lumen includes a generally concave inner wall 100 and a generally convex outer wall 108 with interconnecting side walls 110 and 112. More rounded walls may be used instead of the straight walls shown in FIG. 9.

FIGS. 10, 11, and 12 are provided to show side views of the cannula 50 with the sharp tip 52 so that the configurations of the openings can be seen. FIGS. 10 and 11 show the vent opening 86 with a rotation between each other of ninety degrees. FIG. 12 shows the open channel or slot 56 formed in the side of the cannula used to feed the medicament opening 70 and permit a higher flow rate.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While variations have been described and shown, it is to be understood that these variations are merely exemplary of the present invention and are by no means meant to be limiting.

I claim:

1. A vial adapter for accessing a vial having a vial closure that includes a pierceable seal located over an opening of the vial, the adapter comprising:

a housing having an attachment device to engage the vial for secure mounting of the vial adapter to the vial;

a body portion having a medicament port and a vent port with a medicament lumen leading to the medicament port and a vent lumen leading to the vent port, the medicament and vent lumina being separate from each other; and a cannula located within the housing having a sharpened tip for piercing the seal of the vial closure to provide access to vial contents, the cannula having a medicament lumen in fluid communication with the body medicament lumen and a vent lumen in fluid communication with the body vent lumen, the cannula medicament lumen and cannula vent lumen having respective openings disposed on the sharpened cannula;

wherein the cannula vent lumen has an inner wall and an outer wall, the inner wall is positioned closer with respect to the cannula medicament lumen than the outer wall is positioned with respect to the cannula medicament lumen, and wherein the cannula vent lumen is at least partially wrapped around the medicament lumen, and wherein the cross-sectional area of the cross-sectional shape of the cannula vent lumen is equal to or greater than the cross-section of the area of a cross-sectional shape of the cannula medicament lumen so that the flow rate of air through the body and cannula vent lumina is at least as great as a flow rate of medicament through the combination of the body and cannula medicament lumina.

2. The vial adapter of claim 1 wherein the generally concave cross-sectional shape of the inner wall of the cannula vent lumen comprises an angulation, a vertex of which is oriented toward the outer wall of the cannula vent lumen.

3. The vial adapter of claim 2 wherein the outer wall of the cannula vent lumen has a generally convex cross-sectional shape.

4. The vial adapter of claim 3 wherein the generally convex outer wall and generally concave inner wall are interconnected by two side walls.

5. The vial adapter of claim 4 wherein the side walls are substantially straight but are not aligned on a radius from longitudinal center line of the sharpened cannula.

6. The vial adapter of claim 1 wherein the cross-sectional shape of the inner wall of the cannula vent lumen comprises linear portions forming an obtuse angle, the vertex of which faces an outer wall.

7. The vial adapter of claim 1 wherein the inner wall of the cannula vent lumen is oriented to face the cannula medicament lumen whereby the cannula vent lumen may be positioned closer to the cannula medicament lumen within the cannula to result in a smaller diameter cannula yet a vent lumen that is at least as large as the medicament lumen.

8. The vial adapter of claim 1 wherein:
the cross-sectional shape of the cannula medicament lumen is generally circular; and
the cross-sectional shape of the inner wall of the cannula vent lumen comprises linear portions forming an obtuse angle, the inner wall oriented to face the cannula medicament lumen;
whereby the cannula vent lumen may be positioned closer to the cannula medicament lumen within the cannula to result in a smaller diameter cannula yet a vent lumen that is at least as large as the medicament lumen.

9. The vial adapter of claim 1 wherein the opening of the cannula vent lumen on the cannula is closer to the sharpened tip than is the opening of the cannula medicament lumen on the cannula.

10. The vial adapter of claim 1 further comprising a needle free valve disposed at the medicament port of the body adapted to control the flow of fluid through the medicament lumina.

11. The vial adapter of claim 1 further comprising a filter disposed at the vent port of the body adapted to control the flow of fluid through the vent lumina.

12. The vial adapter of claim 11 wherein the filter comprises an hydrophilic filter.

13. The vial adapter of claim 11 wherein the filter comprises an anti-bacterial filter.

14. The vial adapter of claim 1 wherein the cannula medicament lumen comprises a cross-sectional shape in the form of a polygon having an inner wall, an outer wall, and at least one side wall interconnecting the inner and outer walls.

15. The vial adapter of claim 14 wherein the cannula medicament lumen is located at a longitudinal centerline of the sharpened cannula.

16. The vial adapter of claim 14 wherein the outer wall of the cannula vent lumen has a generally convex cross-sectional shape.

17. The vial adapter of claim 16 wherein the generally convex outer wall and generally concave inner wall are interconnected by two side walls.

18. The vial adapter of claim 17 wherein the side walls are substantially straight but are not aligned on a radius from a longitudinal center line of the sharpened cannula.

19. The vial adapter of claim 14 wherein the generally concave inner wall shape of the cross section of the cannula vent lumen includes at least one angulation facing the outer wall.

20. The vial adapter of claim 3 wherein the connecting side wall is non-radial in relation to a longitudinal center line of the sharpened cannula.

21. The vial adapter of claim 1 further comprising an open channel formed longitudinally in an outer surface of the cannula from approximately the sharp tip to be in fluid communication with the medicament opening.

22. A method for accessing a vial having a vial closure that includes a pierceable seal located over an opening of the vial, the method comprising:
piercing the seal with a sharpened cannula having a medicament lumen and a vent lumen separate from each other wherein the cannula vent lumen has an inner wall and an outer wall, the inner wall is positioned closer with respect to the cannula medicament lumen than the outer wall is positioned with respect to the cannula medicament lumen, and wherein the cannula vent lumen is at least partially wrapped around the medicament lumen, and the cross sectional area of the cross-sectional shape of the vent lumen is equal to or greater than the cross-sectional area of the cross-sectional shape of the medicament lumen so that the flow rate of air through the vent lumen is at least as great as a flow rate of medicament through the medicament lumen;
mounting a housing having an attachment device to the vial to secure the vial adapter to the vial and the sharpened cannula through the seal, the sharpened cannula being disposed within the housing; and
communicating fluid through the sharpened cannula and through a body portion that is in fluid communication with the cannula, the body portion having a body medicament lumen in fluid communication with the cannula medicament lumen and having a medicament port, and a body vent lumen in fluid communication with the cannula vent lumen and having a vent port, the body medicament and vent lumina being separate from each other.

23. The method of claim 22 further comprising controlling the flow of fluid through the medicament port of the body with a needle free connector having a valve.

24. The method of claim 22 further comprising controlling the flow of fluid through the body portion with a filter disposed in communication with the vent port.

25. The method of claim 24 wherein the step of controlling the flow of fluid comprises controlling the flow of liquid through the body with an hydrophobic filter mounted in communication with the vent port.

26. The method of claim 24 wherein the step of controlling the flow of fluid comprises controlling the flow of airborne agents through the body with an anti-bacterial filter mounted in communication with the vent port.

27. A vial adapter for accessing a vial having a vial closure that includes a pierceable seal located over an opening of the vial, the adapter comprising:
a body portion having a medicament port and a vent port with a medicament lumen leading to the medicament port and a vent lumen leading to the vent port, the medicament and vent lumina being separate from each other; and a cannula mounted to the body and having a sharpened tip for piercing the seal of the vial closure to provide access to vial contents, the cannula having a medicament lumen in fluid communication with the body medicament lumen and a vent lumen in fluid communication with the body vent lumen, the cannula medicament lumen and cannula vent lumen having respective openings disposed on the sharpened cannula;

wherein the cannula vent lumen has an inner wall and an outer wall, the inner wall is positioned closer with respect to the cannula medicament lumen than the outer wall is positioned with respect to the cannula medicament lumen, and wherein the cannula vent lumen is at least partially wrapped around the medicament lumen, and wherein the cross-sectional area of the cross-sectional shape of the cannula vent lumen is equal to or greater than the cross-sectional area of a cross-sectional shape of the cannula medicament lumen so that the flow rate of air through the body and vent lumina is at least as great as a flow rate of medicament through the combination of the body and cannula medicament lumina.

28. The vial adapter of claim 27, wherein the cannula further comprises a slot formed in a side of the cannula from the sharpened tip to the cannula medicament lumen opening to guide fluid to the cannula medicament lumen opening.

29. The vial adapter of claim 1, wherein the cannula further comprises:
a slot formed in a side of the cannula from the sharpened tip to the cannula medicament lumen opening to guide fluid to the cannula medicament lumen opening.

30. The method of claim 22, further comprising:
guiding fluid to the cannula medicament lumen opening using a slot formed in a side of the cannula to a cannula medicament opening.

* * * * *